(12) United States Patent
Chalupa et al.

(10) Patent No.: US 9,326,540 B2
(45) Date of Patent: May 3, 2016

(54) METHOD AND APPARATUS FOR VITAMIN D ENHANCEMENT IN MUSHROOMS

(71) Applicant: Oakshire Holdings, Inc., Kennett Square, PA (US)

(72) Inventors: William F. Chalupa, Landenberg, PA (US); Gary M. Schroeder, Landenberg, PA (US)

(73) Assignee: Oakshire Holdings, Inc., Kennett Square, PA (US)

( * ) Notice: Subject to any disclaimer, the term of this patent is extended or adjusted under 35 U.S.C. 154(b) by 889 days.

(21) Appl. No.: 13/628,194

(22) Filed: Sep. 27, 2012

(65) Prior Publication Data

US 2014/0088049 A1  Mar. 27, 2014

(51) Int. Cl.
*A23L 1/28* (2006.01)
*A23L 1/303* (2006.01)
*A23L 1/025* (2006.01)

(52) U.S. Cl.
CPC .................. *A23L 1/28* (2013.01); *A23L 1/0252* (2013.01); *A23L 1/303* (2013.01)

(58) Field of Classification Search
CPC ......... A23L 1/28; A23L 1/303; A23L 1/0252; A23L 1/0257
See application file for complete search history.

(56) References Cited

U.S. PATENT DOCUMENTS

| 4,892,821 | A | 1/1990 | Omura et al. |
|---|---|---|---|
| 2003/0082072 | A1 | 5/2003 | Koji et al. |
| 2004/0016887 | A1 | 1/2004 | Fink et al. |
| 2004/0115791 | A1 | 6/2004 | Sim et al. |
| 2005/0287255 | A1 | 12/2005 | Notermans |
| 2006/0280753 | A1 | 12/2006 | McNeary |
| 2008/0138469 | A1 | 6/2008 | Degre et al. |
| 2009/0269441 | A1 | 10/2009 | Beelman et al. |
| 2009/0274806 | A1 | 11/2009 | Schroeder |
| 2009/0304880 | A1 | 12/2009 | Kidder et al. |
| 2010/0223843 | A1 | 9/2010 | Williams |

(Continued)

FOREIGN PATENT DOCUMENTS

| CN | 101057658 A | 10/2007 |
|---|---|---|
| CN | 101904497 A | 12/2010 |

(Continued)

OTHER PUBLICATIONS

*Pulsed UV . . . Technology*, 3 pages, Xenon Corporation.

(Continued)

*Primary Examiner* — Steven Leff
(74) *Attorney, Agent, or Firm* — Panitch Schwarze Belisario & Nadel LLP (57) ABSTRACT

An apparatus and method for increasing Vitamin D content in mushrooms is disclosed. A mushroom slurry of comminuted or pulverized mushrooms or mushroom parts and liquid, such as water, is passed under a UV light source and subjected to one or more pulses of UV light. The slurry may be conveyed to the UV light source by a vibrating conveyor. After UV light exposure, the treated slurry may be dried and ground into a powder, or the treated slurry may be filtered and the insoluble portion may be dried and ground into a powder. The irradiated mushroom powder has a mass fraction of Vitamin D2 of at least 2500 IU/gram of powder, and more preferably at least 20,000 IU/gram of powder. Irradiated mushroom powder may be incorporated into consumable food product for humans or animals, and/or may be incorporated into topical preparations for cosmetic use.

17 Claims, 4 Drawing Sheets

(56) References Cited

U.S. PATENT DOCUMENTS

| | | |
|---|---|---|
| 2011/0091579 A1 | 4/2011 | Hausman |
| 2011/0159146 A1 | 6/2011 | Eklund-Jonsson et al. |
| 2012/0247007 A1 | 10/2012 | Verdellen et al. |
| 2012/0288589 A1 | 11/2012 | Chalupa et al. |

FOREIGN PATENT DOCUMENTS

| | | |
|---|---|---|
| CN | 101904498 A | 12/2010 |
| DE | 102005031362 A1 | 1/2007 |
| DE | 20 2010 016 402 U1 | 2/2011 |
| JP | 55015766 A | 2/1980 |
| JP | 57189660 A | 11/1982 |
| JP | 59021367 A | 2/1984 |
| JP | 4183369 A | 6/1992 |
| JP | 5078201 A | 3/1993 |
| JP | H05-153935 A | 6/1993 |
| JP | 6062764 A | 3/1994 |
| JP | 7194369 A | 8/1995 |
| JP | 8051927 A | 2/1996 |
| JP | 10229846 A | 9/1998 |
| JP | 11000046 A | 1/1999 |
| JP | 11056288 A | 3/1999 |
| JP | 2000157045 A | 6/2000 |
| JP | 2004222627 A | 8/2004 |
| JP | 2006230327 A | 9/2006 |
| JP | 2007236442 A | 9/2007 |
| KR | 100322481 B1 | 1/2002 |
| KR | 20030040258 A | 5/2003 |
| KR | 20030083500 A | 10/2003 |
| KR | 20030087209 A | 11/2003 |
| KR | 20030087210 A | 11/2003 |
| KR | 100637833 B1 | 10/2006 |
| KR | 20080008790 A | 1/2008 |
| KR | 20110043224 A | 4/2011 |
| KR | 20110090180 A | 8/2011 |

OTHER PUBLICATIONS

*Xenon Flash Lamp*, 7 pages, retrieved from wikipedia.org.

Viraj J. Jasinghe, et al., *Ultraviolet Irradiation: The Generator of Vitamin D2 in Edible Mushrooms*, 6 pages, www.elsevier.com/locate/foodchem.

Feeney, Mary Jo, *Optimizing Vitamin D2 in Mushrooms, Report of a Pilot Study to Expose Mushrooms to Ultraviolet Light*, 6 pages, Mushroom News, May 2006.

Medallion Labs, Final Report dated Feb. 7, 2008.

Medallion Labs, Final Report dated Mar. 26, 2008.

Medallion Labs, Final Report dated Apr. 18, 2008.

Feeney, M.J., *Mushrooms and Health Global Initiative Bulletin*, Nov. 2009, pp. 1-12.

Calvo, M.S., et al., *Vitamin D fortification in the United States and Canada: current status and data needs*, Am. J. Clin. Nutr., 2004 American Society for Clinical Nutrition, pp. 1710S-1716S.

Jasinghe, V.J., et al., *Distribution of ergosterol in different tissues of mushrooms and its effect on the conversion of ergosterol to vitamin D2 by UV irradiation*, Food Chemistry 92, 2005, pp. 541-546.

Lee, J., et al., "The Effect of UV-B Irradiation and Hot-Air Drying on the Vitamin D2 Contents of Shiitake Mushroom (*Lentinus edodoes*)" (2002), 18(2), Korean J. Soc. Food Cookery Sci., pp. 173-178.

Kawazoe, K., et al., *Producing Vitamin D2-Fortified Shiitake Mushroom Powder Using Ultraviolet Irradiation Device* (1997), vol. 44, No. 6, Nippon Shokuhin Kagaku Kogaku Kaishi Technology Report, pp. 442-446.

Int'l Preliminary Report on Patentability issued Apr. 9, 2015 in Int'l Application No. PCT/US2013/059862.

Chikthimmah, N., et al., *Microbial Spoilage of Fresh Mushrooms* (2006), Microbiology of Fruits and Vegetables, Taylor & Francis Group, LLC, pp. 135-158.

XP-002716683, Thomson Scientific, AN 2011-A34475, Dec. 8, 2010.

METHOD AND APPARATUS FOR VITAMIN D ENHANCEMENT IN MUSHROOMS

BACKGROUND OF THE INVENTION

1. Field of the Invention

This invention relates to a method and apparatus for increasing Vitamin D content in a mushroom slurry comprising a fluid, such as water, and fresh mushrooms, or mushroom parts, spawn and/or mycelia. The slurry is exposed to a broad spectrum of light for a specified period of time, using an electric glow discharge lamp. The slurry then is filtered to remove excess water and undesirable soluble materials. The remaining filter cake is dried and ground into a powder. The resulting mushroom powder has high levels of Vitamin D2, and is all natural, vegetarian, and can be used as an ingredient to fortify foods.

2. Description of the Prior Art

The two major forms of Vitamin D are Vitamin D2 and D3. Vitamin D2 is not produced by the human body and is only derived from fungi and plant sources. Vitamin D3 is produced in human skin through exposure to sunlight. The benefits of Vitamin D are numerous, and deficiency of the vitamin in humans can lead to several diseases. Because human exposure to sunlight for prolonged periods is impractical, in order to receive the benefits and overcome potential deficiencies of Vitamin D, there is a need for a method and an apparatus to increase Vitamin D2 in mushrooms and in dried mushroom powder to create a foodsource for this important vitamin.

Commercially grown mushrooms contain very low levels of Vitamin D2, typically less than 20 International Units (IU) per 85 gram standard fresh serving. 40 IU of Vitamin D2 equals 1 microgram. Mushrooms, however, naturally contain ergosterol, a biological precursor to Vitamin D2. Research shows that ergosterol in several species of mushrooms converts to Vitamin D2 when exposed to UV light. White button mushrooms, brown portobello mushrooms, shiitake mushrooms, and oyster mushrooms are some types of mushrooms known to show a Vitamin D2 response when exposed to UV light. With sufficient duration and exposure, the level of Vitamin D2 in these and other mushroom species can reach or exceed 400 IU/85 g of fresh mushrooms, equating to 100% of the current recommended Daily Value for Vitamin D in the United States.

To increase Vitamin D level in mushrooms, certain methods in the background art require mushroom exposure to UV light for extended periods to achieve a significant increase in the level of Vitamin D. In one method, exposure times from 1 hour to 24 hours were required. In other methods, 20 minutes to 60 minutes of exposure time were required. See Jasinghe, V. J., Perera, C. O., "Distribution of ergosterol in different tissues of mushrooms and its effect on the conversion of ergosterol to vitamin D2 by UV irradiation," *Food Chem.* (2005), 92, pp. 541-46; Jasinghe, V. J., Perera, C. O., "UV irradiation: The generator of Vitamin D2 in edible mushrooms," *Food Chem.* (2006), 95, pp. 638-43; and Jasinghe, V. J. "Conversion of ergosterol in edible mushrooms to Vitamin D2 by UV radiation," Thesis submitted to the Department of Chemistry, National University of Singapore (2005).

The prior work to increase Vitamin D content in mushrooms relates to treating fresh mushrooms with UV light. Photolytic treatment of dried mushroom powder to produce high levels of Vitamin D2 has also been taught. Alternative methods for treating commercially viable quantities of mushrooms for short treatment times to produce foods or food additives with high Vitamin D2 content continue to be sought.

SUMMARY OF INVENTION

One embodiment of the present invention is a method for increasing Vitamin D content of mushrooms by treating a mushroom slurry formed of mushroom particles suspended in a liquid. The mushroom slurry having mushroom particles of particle sizes of about 200 microns or less is irradiated with one or more pulses of ultraviolet light with wavelengths in the range of about 200 to about 800 nanometers emitted by an electric glow discharge lamp, such as a xenon lamp. Preferably, the mushroom particle sizes in the mushroom slurry are about 100 microns or less before the slurry is irradiated. Ideally, the mushroom slurry is vibrated as it is irradiated.

After irradiating, the mushroom slurry may be dried and the remaining solids ground to form a powder. More preferably, after irradiating, the mushroom slurry is filtered to remove excess liquid. The remaining filter cake is dried and ground into a powder. The resulting irradiated mushroom powder has a Vitamin D2 level of at least 2500 IU/gram, preferably at least 7500 IU/gram, and most preferably at least 20000 IU/gram. This irradiated mushroom powder may be used as a condiment to be sprinkled on or into foods, or may be incorporated into a consumable food product, including food for human consumption as well as animal feed. The irradiated mushroom powder alternatively may be incorporated into topical preparations for cosmetic use.

The mushroom powder may be made from one or more mushrooms of various types, including but not limited to, white button mushrooms, brown portobello mushrooms, shiitake mushrooms, maitake mushrooms, oyster mushrooms, *agaricus bisporus*, and mixtures thereof.

The mushroom slurry is prepared by combining fresh mushrooms or mushroom pieces or particles with a liquid, such as water, and then passing the mixture through a high shear mixer or a pressure reactor, such as a homogenizer, or both a high shear mixer and a pressure reactor. The pressure reactor is preferred as it is able to rupture or destroy individual cell walls of the mushroom tissue thus releasing the contents of the cells into the slurry liquid. The pressure reactor uses a combination of pressure drop to explode the cell walls as the mushroom slurry is passed through a chamber, followed by contacting the slurry with a window or wall within the chamber to further ensure cell destruction. This greater communition or pulverizing of the mushroom tissues in the slurry allows for greater efficiency of converting ergosterol to Vitamin D2 using a pulsed light.

The pulsed light preferably is an electric glow discharge lamp capable of emitting pulses of light with wavelengths in the range of about 200 to about 800 nanometers, such as a xenon lamp. Preferably, the electric glow discharge lamp is enclosed in a light chamber that is provided with means for controlling temperature therein, such as a blower and exhaust. A conveyor may convey the mushroom slurry for exposure to one or more pulses of light by the lamp. Preferably, the conveyor is a type that shakes or vibrates the mushroom slurry as it is conveyed for exposure to radiation. Examples are vibrating conveyors, shaker tables, vibrating pans and vibrating chutes. The UV light-treated slurry may be collected and recirculated one or more times for further exposure to UV light pulses.

A batch type system also can be used in which a vessel is equipped with a UV or pulsed light that is submerged in the mushroom slurry or is fixed to the sides of the vessel. The slurry is then mixed or agitated for a fixed period of time to convert the ergosterol to Vitamin D.

After the slurry has been exposed to the UV light source for one or more passes, it may be dried to remove the liquid. The dried solids may then be ground into powder. More preferably, after the slurry has been exposed to the UV light source, the slurry is filtered to separate the insoluble fraction from the soluble fraction. The soluble materials do not contain high levels of Vitamin D and may be discarded. Vitamin D is water insoluble and by removing the water soluble portions of the slurry the remaining insoluble portion now contains extremely high levels of Vitamin D. The insoluble portion, or filter cake is then dried and ground into a powder.

DETAILED DESCRIPTION OF THE PREFERRED EMBODIMENTS

As a first step, fresh mushrooms are cultivated using traditional methods. After harvesting, any part of the mushroom can be used including stems, caps, stumps, waste material from the slicing process, or culls otherwise unfit for sale to the fresh market.

The growing medium used to produce the mushrooms can also be considered a raw material source for production of animal feed type products. The seed or source material used to grow mushrooms commonly referred to as spawn can also be used.

Figure 3:
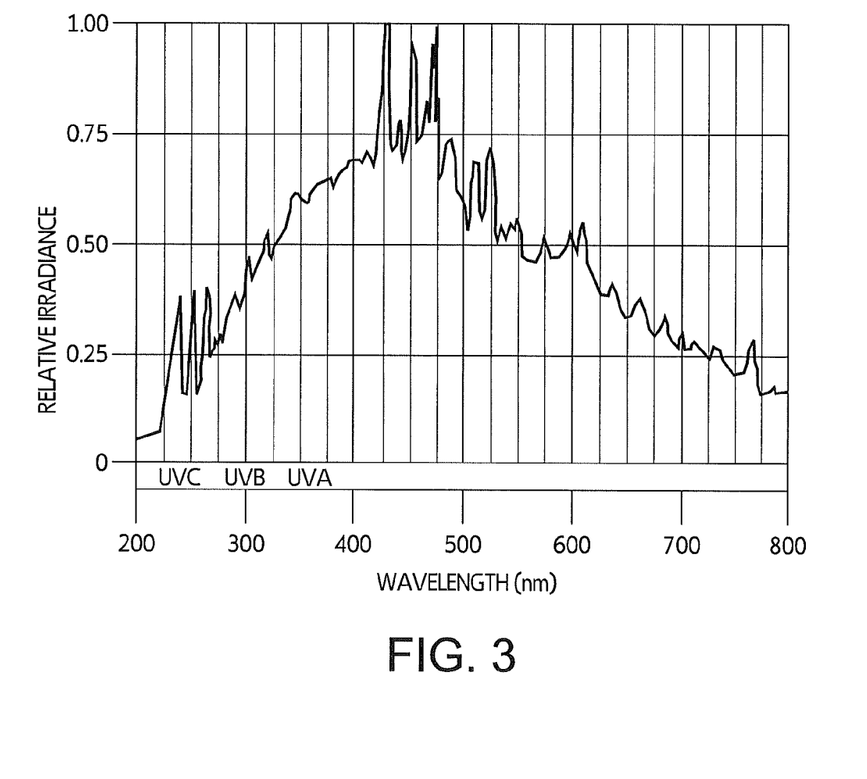
FIG. 3 is a representative plot of relative irradiance versus wavelength of light that is generated by a xenon pulsed UV light emitting electric glow discharge lamp.
Figure 4:
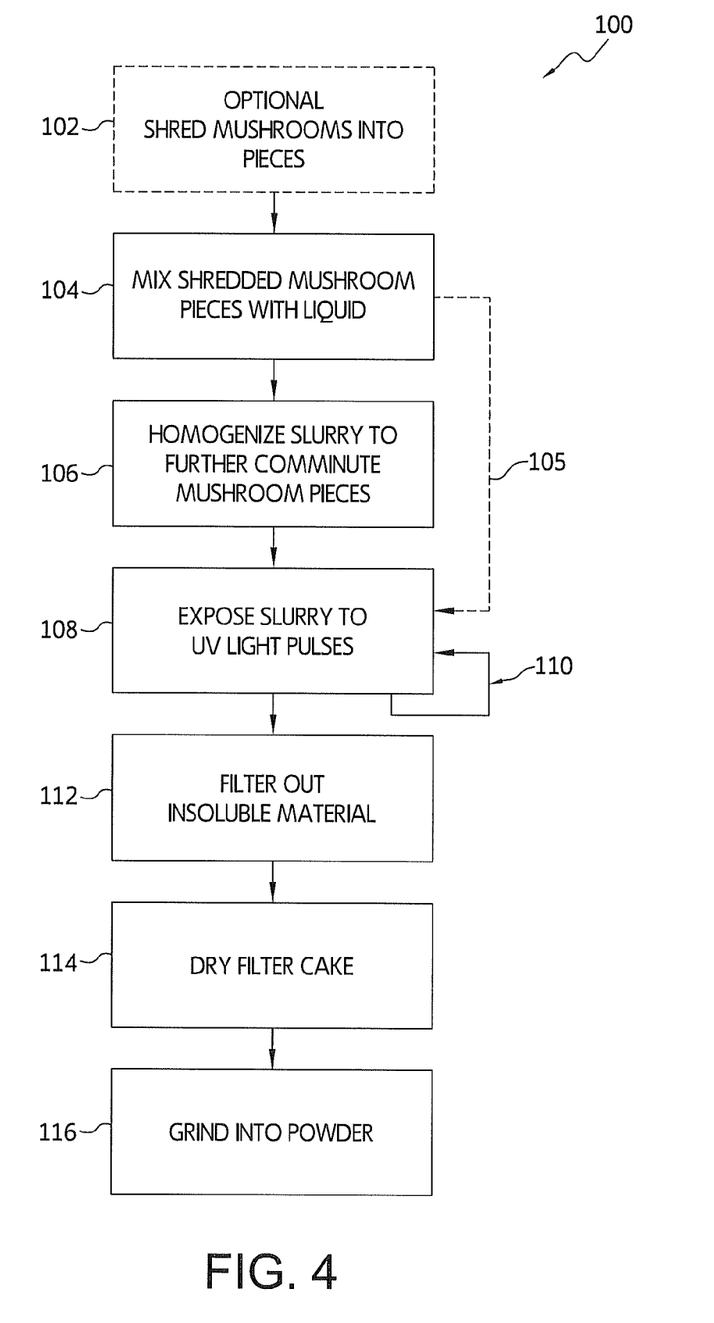
FIG. 4 is a flowchart diagram of one method increasing the Vitamin D content of mushrooms.

Referring now to FIG. 4, the whole mushrooms or mushroom pieces are shredded into pieces as an optional first step 102. Next, the mushroom pieces are combined with a suitable liquid or fluid, such as water or water mixed with ethanol or water mixed with propylene glycol, using a high shear mixer to produce a slurry (step 104 in FIG. 3). Suitable high shear mixers include models BX60 and DX60 from Silverson Mixer of Massachusetts. The mushroom slurry also may be formed using a Waring blender or a colloid type mill.

Preferably, the slurry is then passed through a pressure reactor or homogenizer capable of producing a pressure drop to explode individual cells contained within the mushroom tissue (step 106 in FIG. 4). While not wishing to be bound by any one theory, it is believed that the cells of the mushroom tissue release their contents, including ergosterol, into the slurry fluid or liquid in such pressure reactor or homogenizer. The high shear mixer may be sufficient to homogenize or emulsify the mushrooms into a flowable slurry. In such a case, the slurry may by-pass the pressure reactor (step 105) in FIG. 4.

Alternatively, or additionally, one or more enzymes may be added to the slurry to break apart or destroy the mushroom cells to disperse cell components into the slurry. Representative enzymes for this purpose include cellulase and chitinase.

Next, the resulting slurry is passed under a pulsed UV light, preferably by means of a vibrating conveyor (step 108 in FIG. 4). Alternatives to the vibrating conveyor include a shaker table, a vibrating pan and a vibrating chute.

The pulsed UV light emits up to three (3) pulses of light per second, and is powerful enough to convert a very high percentage of ergosterol present in the slurry to vitamin D. Longer exposure times to the pulsed light appear to produce higher ergosterol conversion to vitamin D. Optionally, the slurry may be recirculated and passed under the pulsed UV light more than one time for more than one exposure (step 110 in FIG. 4).

We have found that particle size can impact the level of Vitamin D that can be achieved in the mushroom slurry. What we discovered is that whatever the UV light source used, the UV exposure only converts ergosterol to vitamin D to a narrow optical depth. Slurries that contain mushroom solids or powders with an average particle size of about 50-75 microns provide optimal results for efficient conversion of ergosterol to Vitamin D2.

Vitamin D is considered a fat soluble vitamin. It is therefore contained in the insoluble portion of the mushroom slurry. After exposure to UV light, the slurry is filtered to separate the soluble and insoluble fractions (step 112 in FIG. 3). The soluble fraction contains primarily dissolved polysaccharides, such as sugars. The insoluble fraction contains primarily chitin, which comprises the cell walls of the mushroom tissue, some proteins, and very high levels of vitamin D. The insoluble fraction, or filter cake, is retained, and the soluble fraction is discarded. Suitable filtering means include standard laboratory grade filter paper, a filter bag with a desired micron size, a filter press and/or a centrifuge.

The filter cake is then dried to produce a shelf stable low moisture product having a moisture content of less than about 30% moisture by weight (step 114 in FIG. 3). This shelf stable low moisture product (mushroom powder) typically has about 8-15% moisture by weight. The filter cake may be dried in a number of ways, including but not limited to a batch type process using air convection, or a fluid bed type dryer, as well as a combination type apparatus that performs drying and grinding simultaneously.

The dried mushroom slurry filter cake then is ground using standard grinding methods to produce a powder with a particle size specific to its intended application (step 116 in FIG. 3). For example, if the intended application is to use the powder at low usage levels to fortify a processed food with Vitamin D, a small particle may be desired. If the intended application of the powder is for use as a condiment or seasoning, a larger particle might be preferred.

The mushroom powder particles preferably will pass through a 10 mesh screen (about 2 mm), more preferably pass through a 20 mesh screen (about 850 microns) and more preferably will pass through a 30 mesh screen (about 600 microns) and most preferably will pass through a 70 mesh screen (about 210 microns.) A 100 mesh product (about 150 microns) is preferred for food processing applications.

Early trials using cheesecloth as the filter media did not produce a significant difference in Vitamin D levels when comparing the soluble and insoluble fractions. Subsequent testing using Whatman laboratory grade filter paper did produce a significant difference in the soluble and insoluble fractions. Ultimately, many different types of filtration methods can be used. The filter method used preferably can filter out particles down to about 1 micron in the insoluble fraction. Any particles smaller than 1 micron pass through the filter and are discarded with the soluble fraction. Besides significantly increasing the Vitamin D content in the insoluble fraction, filtration of the slurry also helps to achieve additional advantages. By removing the majority of the water from the insoluble fraction, drying times are significantly reduced allowing for a large savings in energy. Filtration also removes a large portion of the soluble sugars, such as mono and disaccharides in addition to polysaccharides, a large portion of which are in the form of mannitol. These materials are very hygroscopic. By removing them from the finished dried powder, a free flowing powder is obtained that is less susceptible to high moisture conditions, thus making a more stable powder product with an increased shelf life.

Many different mushroom species can be processed in a slurry to convert ergesterol to Vitamin D. Our results suggest that all mushroom species we have evaluated can be used, specifically including, but not limited to, white button, *agaricus bisporus*, shiitake, oyster, maitake, and mixtures thereof.

Figure 1:
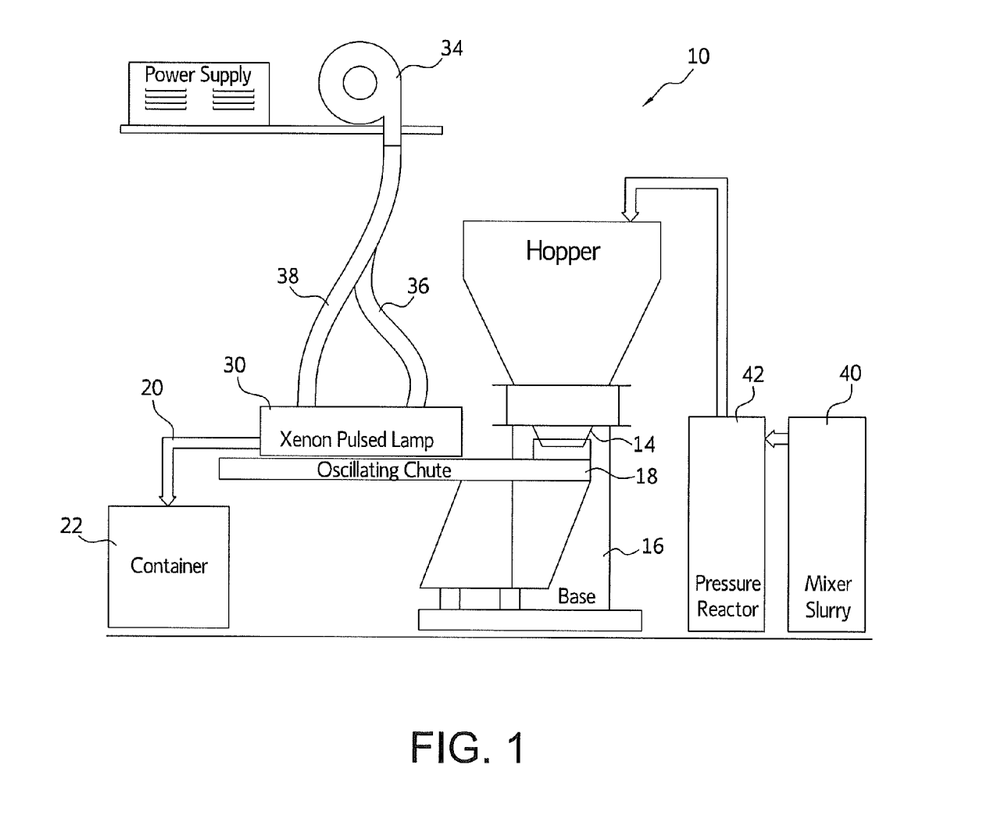
FIG. 1 is a schematic front elevational view of an apparatus for treating a mushroom slurry with UV radiation.

Referring next to FIG. 1, an apparatus 10 for increasing Vitamin D content in mushroom slurry is shown schematically. Mushrooms and mushroom pieces are shredded, comminuted or pulverized in a mixer 40. A liquid or fluid, such as water, is mixed with the shredded mushrooms to form a mushroom slurry. The mushroom slurry is introduced to a homogenizer or pressure reactor 42 to further pulverize or separate the mushroom pieces into smaller particles or components within the mushroom slurry. The homogenized mushroom slurry is introduced into a hopper 12 that is mounted on a base 16. The hopper 12 terminates in a funnel or exit portion that pours the mushroom slurry 20 onto a vibratory conveyor or oscillating chute 18. The conveyor conveys the mushroom slurry 20 into a light chamber 30 that houses an electric glow discharge lamp, such as a xenon pulsed lamp (not shown in FIG. 1).

To control temperature within the light chamber 30, air may be blown into the light chamber 30 using a blower 34. Connected to the blower 34 is an intake hose 36 used to force air into the light chamber 36. The forced air is then removed from the light chamber 30 using an outlet hose 38. We found that it is beneficial, and in some embodiments, necessary, to use the blower 34 because the lamp can generate so much heat that, without the forced air ventilation and cooling, components of the lamp and illumination assembly can melt or otherwise become inoperative. The forced air ventilation also helps control the temperature of the mushroom slurry so that it does not burn or cook.

The conveyor conveys the mushroom slurry through the light chamber 30 while the lamp directs UV light radiation onto the mushroom slurry. The conveyor oscillates or vibrates or shakes to distribute the mushroom slurry on the conveyor, and to direct the radiation onto a significant portion of the surface area of the slurry. In this embodiment, the conveyor vibrates at a rate between 1 Hz and 50 Hz, and is adjusted so that the slurry passes through the illumination chamber in 6 seconds. Since the lamp pulses 3 times per second, the slurry receives 18 pulses while traversing through the illumination chamber. If it is desired to expose the mushroom slurry to more than 18 pulses, the slurry can be collected and recirculated or passed two or more times through the illumination chamber. Alternatively, two or more illumination chambers can be used so the slurry passes, in series, through the two or more illumination chambers.

The irradiated mushroom slurry 20 is then deposited into a container 22 as desired.

A more intense UV light-emitting source was found to increase processing speed. Intense bursts of light can be emitted from pulsed lamps made with xenon gas. These pulses of light from xenon lamps occur in less than 2 milliseconds and create a broad spectrum of UV light. One type of xenon pulse lamp that has been used is Model RC-747-16 manufactured by Xenon Corporation. This xenon pulse lamp, delivers at least 505 joules total light energy per pulse. FIG. 3 illustrates the spectrum for the Model RC-747-16 xenon pulse lamp. This type of high intensity lamp emits pulses of UV radiation with an intensity of at least 1.26 J/cm$^2$ at 1" from the window face of the lamp.

Preferably, the UV radiation emitted by the UV light-emitting source has wavelengths in the range of about 200 to about 800 nanometers. Without intending to be limiting as to mechanism, we believe that it is UV-B radiation which is most effective in the photoisomerization of ergesterol to Vitamin D2.

Figure 2:
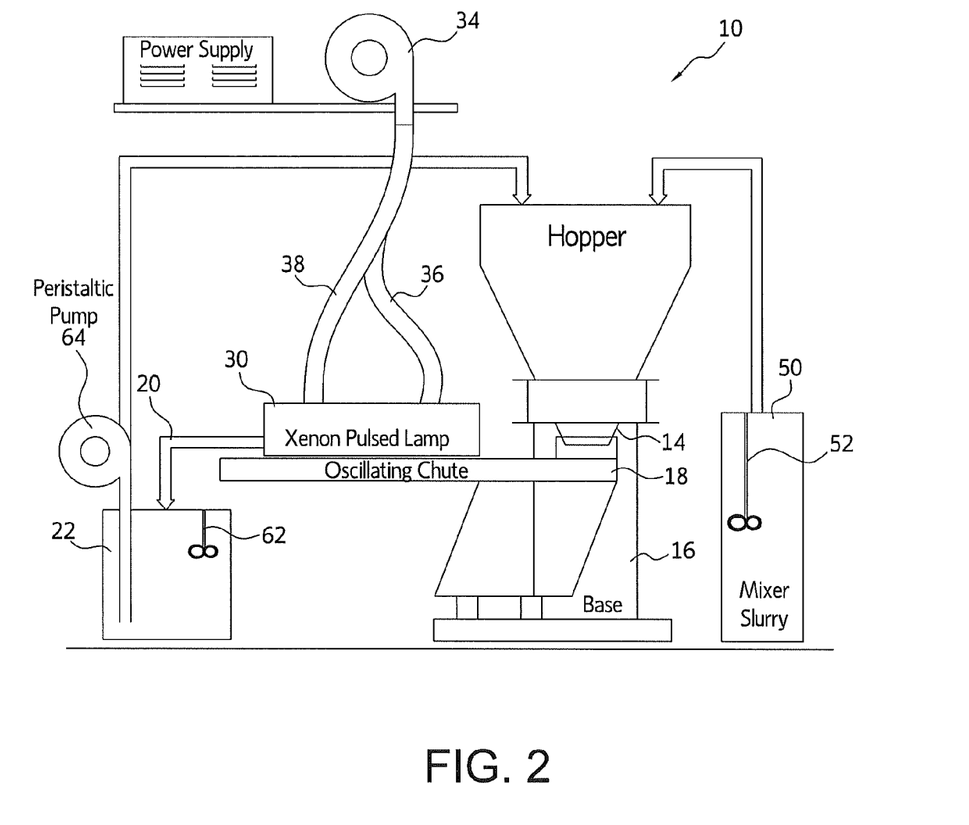
FIG. 2 is a schematic front elevational view of an alternative apparatus for treating a mushroom slurry with UV radiation.

Referring next to FIG. 2, an alternative apparatus 10A for increasing Vitamin D content in mushroom slurry is shown schematically. In FIG. 2, like structures have the same reference numerals as the apparatus 10 in FIG. 1 and operate in like fashion. Different from the apparatus 10 in FIG. 1, in FIG. 2, the apparatus 10A omits the pressure reactor. Instead, a mixer 50 forms a slurry by mixing a liquid or fluid and mushrooms. A suitable high shear mixer is a Silverson high shear mixer with changeable mix-heads 52, including a general purpose disintegrating attachment, or a square hole high shear attachment or an emulser head and screen. The different mix-heads may be attached at various stages of mixing to form a flowable slurry or emulsion.

Another variation as shown in FIG. 2, the container 22 includes a propeller mixer 62 to keep mixing the slurry after it exits the light chamber 30. The treated slurry may be pumped using a positive displacement pump 64, such as a peristaltic pump, for recirculating the treated slurry to the light chamber for another pass under the UV-light source.

The FDA has ruled on the safety of food exposed to xenon lamp pulsed light exposure.

Food and Drug Administration Issues Approval for Pulsed UV Light in the Production, Processing and Handling of Food Code 21CFR179.41, issued by the Food and Drug Administration (FDA), Department of Health and Human Services, approves the use of Pulsed UV light in the production, processing and handling of food.

Title 21—FOOD AND DRUGS (Page 438)

Chapter I—FOOD AND DRUG ADMINISTRATION, DEPARTMENT OF HEALTH AND HUMAN SERVICES Part 179—IRRADIATION IN THE PRODUCTION, PROCESSING AND HANDLING OF FOOD Subpart B—Radiation and Radiation Sources Sec. 179.41 Pulsed light for the treatment of food Pulsed light may be safely used for the treatment of foods under the following conditions:

(a) The radiation sources consist of xenon flashlamps designed to emit broadband radiation consisting of wavelengths covering the range of 200 to 1,000 nanometers (nm), and operated so that the pulse duration is no longer than 2 milliseconds (ms);

(b) The treatment is used for surface microorganism control;

(c) Foods treated with pulsed light shall receive the minimum treatment reasonably required to accomplish the intended technical effect; and (d) The total cumulative treatment shall not exceed 12.0 joules/square centimeter (J/cm\2\.)

The FDA guideline uses pulsed light for surface microorganism control. Mushrooms that are exposed to xenon lamp radiation for 2 milliseconds are within the FDA guideline for food safety. Surprisingly, this short duration exposure can be sufficient to achieve significant enhancement of Vitamin D in mushrooms.

As the mushroom slurry traverses the UV light exposure area so as to expose most or all of the individual particles to UV light, significantly higher levels of Vitamin D are achieved. After further processing through filtration, drying and grinding the resulting powder has a very high level of Vitamin D. The powder can now economically be used as an all natural, vegetarian source of Vitamin D2 in processed food products at very low usage levels without dramatically affecting the flavor, appearance, or cost of the finished product. The powder also may have use in animal feed. The powder also may be incorporated into preparations for topical application to the skin, scalp or hair.

In summary, the apparatus and methods disclosed herein permit continuous and economic production of mushroom powder with extremely high levels of vitamin D2 on a commercial scale.

EXAMPLES

Example 1

Whole mushrooms of the species *agaricus bisporus* are combined with an equal weight of water and mixed or homogenized into a puree using a Waring blender. The resulting mushroom slurry has suspended mushroom particles with an average particle size of 150-200 microns. The mushroom slurry then is circulated under a pulsed UV light model RC-747-16 manufactured by Xenon Corporation. The mushroom slurry is dried and ground into a powder. The resulting mushroom powder has a mass fraction of Vitamin D2 contains at least 10,000 IU/gram of powder.

Example 2

Mushroom slurry is produced as in Example 1 and then passed through a pressure reactor model DR-HP-3 with a 0.03" orifice operating at 3000 psi manufactured by IKA Corporation. The pressure reactor destroys or ruptures the individual cell walls of the mushroom tissue allowing for more ergosterol to react with the pulsed UV light. The pressure reactor produces a slurry with suspended mushroom particles having an average particle size of 50-100 microns. The mushroom slurry then is circulated under the pulsed UV light as in Example 1. The mushroom slurry is dried and ground into a powder. The resulting mushroom powder has a mass fraction of Vitamin D2 of at least 20,000 IU/gram of powder.

Example 3

Mushroom slurry is produced as in Example 2. After circulating the mushroom slurry under the pulsed UV light, it is filtered to separate the soluble and insoluble fractions. The soluble fraction contains mostly dissolved polysaccharides does not contain significant level of Vitamin D2 and is discarded. The insoluble fraction, or filter cake, is retained, dried and ground into a powder. The resulting mushroom powder has a mass fraction of Vitamin D2 of at least 40,000 IU/gram of powder.

Example 4

Mushroom stumps and root material are combined with an equal weight of water and mixed or homogenized into a slurry using a Waring blender. The mushroom slurry is passed through a pressure reactor model DR-HP-3 manufactured by IKA Corporation. The pressure reactor has a 3-stage chamber with the following combination: 0.03" orifice with a ½ A window, followed by a 0.05" orifice with no window, followed by a 0.055" orifice with full windows. The 3-stage chamber allows for greater cell wall destruction. The slurry then is circulated under the pulsed UV light, filtered and dried. The resulting powder produced from the stumps and root material has a mass fraction of Vitamin D2 of at least 15,000 IU/gram of powder.

Example 5

Whole mushrooms are combined with an equal weight of water and mixed or homogenized into a slurry using a Silverson DX60 mixer. A standard general purpose disintegrating head is used at first. Then, a square hole high shear mix head is used. Finally, an emulser head and screen is used with the mixer. The resulting mushroom slurry comprises partices with particle sizes of from 50 to 100 µm. The slurry then is circulated under the pulsed UV light, filtered and dried. The resulting mushroom powder has a mass fraction of Vitamin D2 of at least 40,000 IU/gram of powder.

TABLE 1

| Sample Description: | Vitamin D IU/gram |
| --- | --- |
| Example 1 | 11,826 |
| Example 2 | 19,758 |
| Example 3 (unseparated) | 14,674 |
| Example 3 (solid portion) | 53,661 |
| Example 3 (liquid portion) | 79 |
| Example 4 | 16,456 |
| Example 5 | 40,000 |

The invention has been illustrated by detailed description and examples of particular embodiments. Various changes in form and detail may be made to the illustrative embodiments without departing from the spirit and scope of the present invention. Therefore, the invention must be measured by the claims and not by the description of the examples or the particular embodiments.

The invention claimed is:

1. A method for increasing vitamin D content of mushrooms, comprising:
   providing a mushroom slurry of mushroom particles suspended in a liquid; and
   irradiating the mushroom slurry with one or more pulses of ultraviolet light with wavelengths in the range of about 200 to about 800 nanometers emitted by an electric glow discharge lamp.

2. The method of claim 1, wherein the electric glow discharge lamp is a xenon lamp.

3. The method of claim 1, further comprising:
   comminuting or pulverizing the mushroom particles into smaller particles in the mushroom slurry.

4. The method of claim 1, further comprising:
   homogenizing the mushroom particles in the mushroom slurry with a blender, a mixer, a colloid type mill or a pressure reactor.

5. The method of claim 1, further comprising:
   breaking apart mushroom cells with one or more enzymes incorporated into the mushroom slurry.

6. The method of claim 1, further comprising:
   conveying the mushroom slurry past the lamp with a conveyor selected from the group consisting of vibrating conveyor, shaker table, vibrating pan and vibrating chute.

7. The method of claim 1, further comprising:
vibrating the mushroom slurry while the mushroom slurry is irradiated.

8. The method of claim 1, further comprising:
separating the mushroom slurry into soluble and insoluble fractions.

9. The method of claim 8, wherein separating is by filtering or centrifuging.

10. The method of claim 8, further comprising:
drying the insoluble fraction to form a filter cake; and
grinding the filter cake to form a powder.

11. The method of claim 10, wherein said mushroom powder has a mass fraction of Vitamin D2 of at least 2500 IU/gram of powder.

12. The method of claim 10, wherein the mushroom powder has a moisture content of less than about 30% moisture by weight.

13. The method of claim 1, wherein the mushroom particles are made from one or more mushrooms selected from the group consisting of: white button mushrooms, brown portobello mushrooms, shiitake mushrooms, oyster mushrooms, *agaricus bisporus*, and mixtures thereof.

14. The method of claim 1, wherein the mushroom particles are made from one or more mushroom components selected from the group consisting of: stumps, root material, and spawn.

15. The method of claim 1, further comprising:
drying the irradiated slurry; and
grinding the dried slurry to form a powder.

16. The method of claim 15, wherein said mushroom powder has a mass fraction of Vitamin D2 of at least 2500 IU/gram of powder.

17. The method of claim 15, wherein the mushroom powder has a moisture content of less than about 30% moisture by weight.

* * * * *